United States Patent [19]
Chase et al.

[11] Patent Number: 5,744,099
[45] Date of Patent: Apr. 28, 1998

[54] APPARATUS FOR TRANSFER OF BIOLOGICAL FLUIDS

[75] Inventors: Eric S. Chase, Walnut Creek; Harvey L. Schulte, Los Altos, both of Calif.

[73] Assignee: Cytek Development Inc., Fremont, Calif.

[21] Appl. No.: 528,847

[22] Filed: Sep. 15, 1995

[51] Int. Cl.[6] .................................................... G01N 35/10
[52] U.S. Cl. ............................ 422/82; 422/81; 422/100; 436/53; 436/174; 436/180
[58] Field of Search .................................. 422/63, 65, 67, 422/73, 81, 100, 104, 82; 436/43, 47, 49, 52, 53, 54, 174, 179, 180; 73/864.01, 864.24, 864.25, 846.34; 141/2, 9, 263

[56] References Cited

U.S. PATENT DOCUMENTS

| | | | |
|---|---|---|---|
| 4,328,185 | 5/1982 | Reasons et al. | 422/82 |
| 4,586,546 | 5/1986 | Mezei et al. | 141/2 |
| 4,609,017 | 9/1986 | Coulter et al. | 141/1 |
| 4,756,201 | 7/1988 | Uffenheimer | 73/864.83 |
| 4,845,025 | 7/1989 | Lary et al. | 435/2 |
| 4,861,553 | 8/1989 | Mawhirt et al. | 422/65 |
| 4,928,539 | 5/1990 | Champseix et al. | 73/864.24 |
| 5,094,961 | 3/1992 | Del Valle et al. | 436/180 |
| 5,104,807 | 4/1992 | Mitsumaki et al. | 436/47 |
| 5,133,392 | 7/1992 | Hamann | 141/1 |
| 5,143,849 | 9/1992 | Barry et al. | 436/50 |
| 5,354,537 | 10/1994 | Moreno | 422/100 |
| 5,439,645 | 8/1995 | Saralegui et al. | 422/64 |

*Primary Examiner*—Long V. Le
*Attorney, Agent, or Firm*—Jim Hillman

[57] ABSTRACT

An apparatus and method is disclosed for transferring biological fluids such as blood and serum from closed containers to multiple receiving containers. The disclosed methods and apparatus perform the transfer of an accurate and precise amount of biological liquid without dilution of the biological liquid, and without splattering of the biological liquid on the walls of the receiving container. Furthermore, the method discloses how to obtain equal concentrations of white blood cells in multiple receiving containers characteristic of their concentration in the sealed container.

19 Claims, 7 Drawing Sheets

APPARATUS FOR TRANSFER OF BIOLOGICAL FLUIDS

FIELD OF THE INVENTION

This invention relates to an improved apparatus and method of aspirating biological liquids from a sealed container and dispensing the liquid to a receiving container.

BACKGROUND OF THE INVENTION

It is desirable to transfer biological liquids from sealed containers to secondary containers in accurate and precise volumes, without diluting the liquid or splattering the liquid on the walls of the receiving container. It is also desirable to transfer formed elements within these fluids, such as blood cells, in accurate and precise numbers. It is also desirable to effect such transfers gently, without damage to formed elements of such liquids. In the art, there are at least two methods to aspirate biological liquids from sealed primary containers to secondary containers in laboratory apparatus. However, neither method achieves all of the desirable features described above.

A state of the art apparatus for transferring biological liquids from primary to secondary containers can be seen in Cavro's MSP 9000. This apparatus consists of an aspiration/dispense probe connected to a syringe pump with a flexible conduit. The aspiration/dispense probe is stainless steel, with a blunt, teflon coated probe tip, as shown in FIG. 7a. The probe assembly is mounted on an apparatus that can move the probe in an x, y, and z direction.

In this method, the conduit and probe are filled with pilot liquid. Then a small amount of pilot liquid is pulled away from the probe tip with the syringe, creating an air gap at the probe tip. The probe then goes down through the septum of a sealed container, to the biological liquid. The sample liquid is aspirated from the primary container into the probe and conduit tubing. The sample liquid is isolated from the pilot liquid by an air gap to prevent dilution of the sample liquid by the pilot liquid. The probe is then moved to a secondary container, and the sample liquid is then dispensed at a high speed by the syringe pump. This high speed dispense provides for kinetic mixing of the dispensed liquid with reagents already in the receiving container. The syringe pump is then stopped nearly instantaneously, and the rapid deacceleration of liquid at the probe tip creates a clean breakoff of sample liquid at the probe tip. This clean breakoff provides for a precise and accurate amount of liquid sample being dispensed.

However, there are four problems with this method. First, the high speed dispense may cause the liquid sample to be splattered on the sides of the secondary container. This splattering results in liquid sample not reacting with subsequent reagents added to the secondary container. Second, the high speed dispense can lead to breakup of the isolating air gap between the liquid sample and pilot liquid, which results in dilution of the sample liquid with pilot liquid.

Third, since the same probe is used to pierce the sealed primary container and dispense to the secondary container, its tip design must be a compromise between the two functions. The optimal design for a seal piercing needle, as shown in FIG. 7b, has a beveled stainless steel tip, with a slight curvature at the tip to prevent coring of the seal. It is not coated with teflon on its outside surface because the teflon would tend to wear off during repeated passages through the seal. The optimal design for a liquid dispense probe, as shown in FIG. 7a, has a flat, non-beveled tip with minimal outlet surface area, and is coated with a nonwettable material such as teflon on its outside surface.

Because a beveled piercing tip has greater outlet surface area than a blunt tip, it is not optimal for dispensing. Also, because a beveled piercing tip cannot be coated by teflon on its outside surface, it is not optimal for dispensing.

Conversely, because a non-beveled tip cannot cut a path through the seal without pushing out a core of seal material into the primary container, it is not optimal for aspirating liquid from a sealed container.

Fourth, the formed elements of blood will travel through the conduit at a velocity generally different than the average velocity of the liquid itself (Cox et. al., Chem. Eng. Sci. 23, 147 (1968). Although a precise amount of blood is dispensed to each receiving container, a nonuniform number of formed elements, such as white cells, will be dispensed to each receiving container.

Hematology analyzers such as Coulter's STKR, described in U.S. Pat. No. 4,609,017, with further refinement in U.S. Pat. No. 5,094,961, use a different approach to transfer an accurate and precise amount of blood from a primary container to a secondary container. In this method, blood is aspirated from a closed container, using a seal piercing needle, into a metering or shear valve, where a precise and accurate amount of blood is isolated. The blood is then flushed out of the metering valve into a secondary container by a diluent. This method has the advantage of sampling a precise and accurate amount of blood from a sealed container, but this method has two disadvantages. It does not have the flexibility of metering variable amounts of blood according to changing user requirements. It also requires a dilution of the blood to flush it from the metering valve. It is well known that the reaction time required for reagents such as monoclonal antibodies to bind to the formed elements of blood is lengthened if the blood is diluted prior to the reaction.

SUMMARY OF THE INVENTION

The invention described herein provides an apparatus and method for the transfer of biological liquids such as blood from a sealed primary container to secondary containers in accurate and precise volumes, without splattering or dilution. This invention also provides for mixing of the dispensed liquid with reagents in the secondary container. This invention also provides for the transfer of formed elements within biological fluids, such as blood cells, in accurate and precise numbers.

The invention consists of three elements; 1) a septum piercing needle to aspirate liquid from a sealed container, 2) a sample storage loop with a) means to isolate the aspirated liquid from the pilot liquid with a gaseous interface, and b) means to transfer the aspirated liquid to a dispense probe, and 3) a dispensing means that a) utilizes the adhesive properties of the aspirated liquid to the secondary container to obtain an accurate and precise volume of dispensed liquid without splattering or dilution, and b) provides for the equal distribution of formed elements within the liquid to multiple receiving containers, such that each receiving container contains a representative number of formed elements per unit volume characteristic of the liquid within the sealed container.

DESCRIPTION OF PREFERRED EMBODIMENTS

Figure 1:
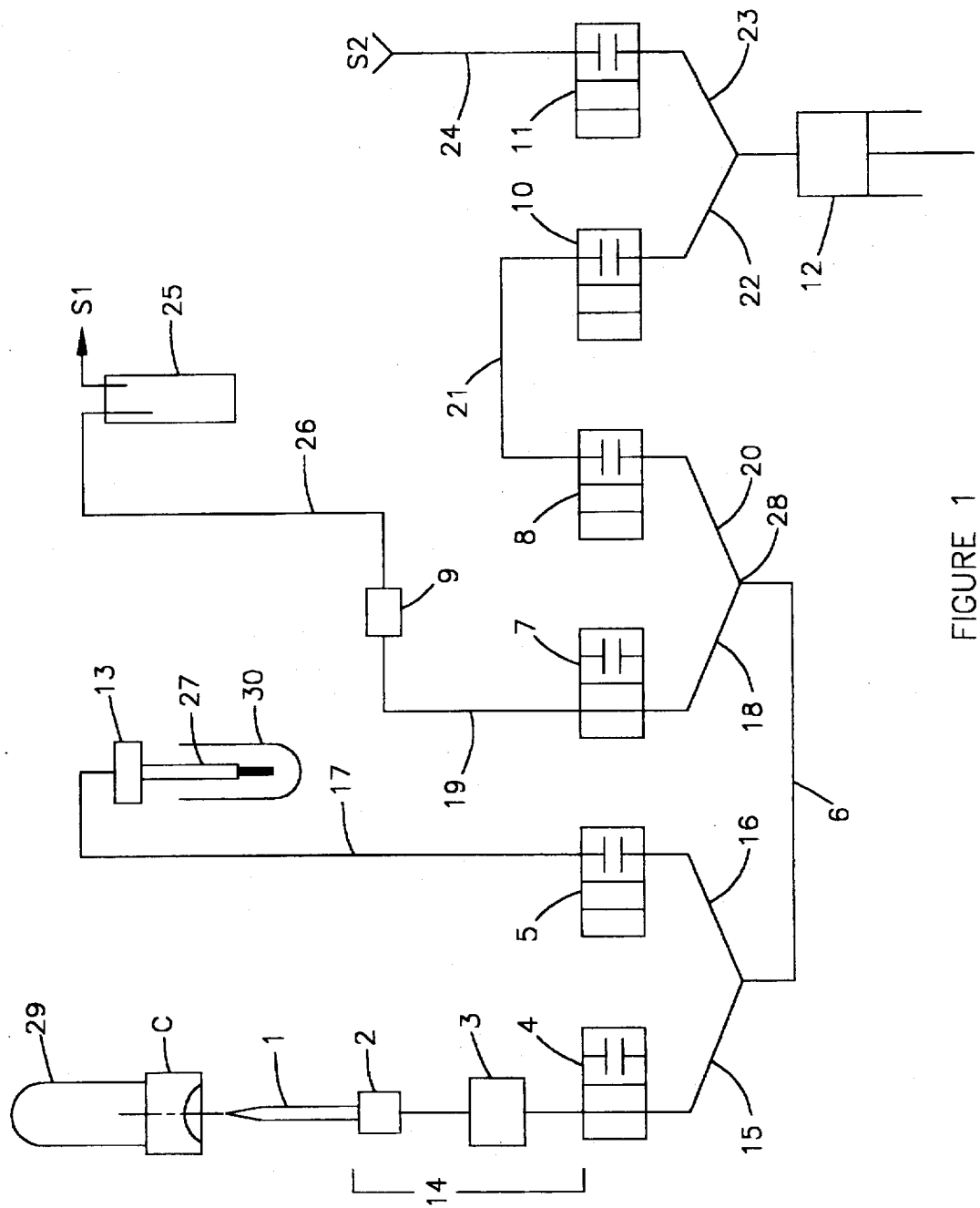
FIG. 1 is a schematic representation of the aspiration and dispensing apparatus.

Refering to FIG. 1, the liquid aspiration cycle from sealed container 29 begins with conduits 14, 15, 16, 17, 6, 18, 19, and 26 filled with air; aspirating needle 1 and dispensing probe 27 filled with air, and conduits 20, 21, 22, 23, and 24 filled with a pilot liquid such as deionized water. Note there is an air/pilot liquid interface 28 at the junction of conduits 18 and 20.

Valves 4, 8, and 10 are open (or unpinched), valves 5, 7, and 11 are closed (or pinched).

Syringe 12 moves down 20 ul, which causes the air/pilot liquid interface 28 at the junction of conduits 18 and 20 to move towards valve 8. This will allow the creation of an gaseous isolation bubble between the aspirated liquid and pilot liquid as described below. Valves 8 and 10 are then closed.

Figure 7A:
FIG. 7a is an illustration of an optimal liquid dispensing probe.
Figure 7B:
FIG. 7b is an illustration of an optimal seal piercing needle.

The aspiration needle 1 is raised through septum C into the sealed container 29 containing sample liquid, and valve 5 is open. The needle is beveled, and is curved at its tip as shown in FIG. 7b to prevent coring of the septum C.

Any vacuum within the sealed container 29 is vented through the aspirating needle 1, conduit 14, Valve 4, conduits 15, and 16, valve 5, conduit 17, and dispense probe 27. Venting of sealed container 29 allows faster vacuum aspiration of liquid from the container, since there may be a residual vacuum within sealed container 29. Valve 5 is then closed, valve 7 is open, and a vacuum is applied to S1 by known methods in the art. The vacuum causes the liquid within sealed container 29 to flow through the aspiration needle 1, conduit 14, Valve 4, conduits 15, 6, and 18, valve 7, conduit 19, and to the sensor 9. When the liquid reaches sensor 9, valve 7 is closed to stop the aspiration of liquid from sealed container 29. An isolation bubble now exists between the aspirated liquid and pilot liquid at the junction of conduits 18 and 20.

Figure 5A:
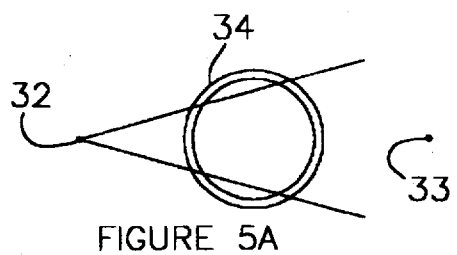
FIG. 5 is a sectional view of the liquid sensor with a) air b) water or serum, and c) blood in the conduit.
Figure 5B:
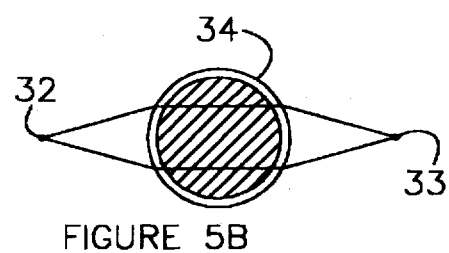
Figure 5C:
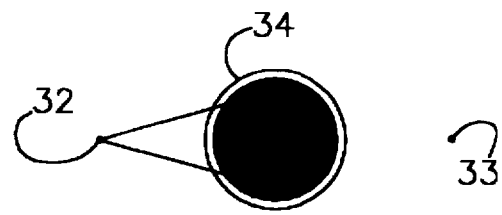

Sensor 9 can distinguish between various fluids within the glass conduit 34 based on the fluids refractive and transmissive propertites. FIG. 5 shows a cross sectional view of the sensor with diverging light source 32, light sensor 33, and glass fluid conduit 34. Conduit 34 can be considered to be a cylinderical lens. Light sensor 33 is placed at the image plane of light source 32. FIG. 5a shows the fluid conduit containing air. Because the refractive index of air is 1.00, there is no refraction of light, and most of the light from source 32 is not seen by the sensor 33. FIG. 5b shows the fluid conduit containing a liquid such as water or serum, which has a refractive index of about 1.33, and transmits a majority of the incident light, Because the refractive index of the conduit is greater than 1.00. light is refracted into the sensor, and most of the light from light source 32 is seen by the sensor 33. FIG. 5c shows the liquid conduit containing a liquid such as blood, which has a refractive index greater than air, and transmits little of the incident light. Although light is refracted by the liquid, most of it is absorbed, and never reaches sensor 33. Thus by measuring the amount of light incident in sensor 33, it is possible to distinguish between air, blood, and serum, if one wishes to dispense serum, and blood is detected, an error message can be given to the user. Likewise, if one wishes to dispense blood, and serum is detected, an error message can be given to the user.

This feature is useful it the sealed container 29 contains a blood layer and serum layer, and it is desriable only to aspirate from the serum layer.

After the liquid has been detected at sensor 9, and valve 7 is closed, valve 5 is then opened. This allows the sealed container 29 to again be vented through dispense probe 27, conduit 17, valve 5, conduits 16 and 15, valve 4, conduit 14, and aspiration needle 1. This venting of sealed container 29 causes aspirated liquid in conduit 15 to backflow into the sealed container 29, thereby clearing particulate matter from filter 3 that may have accumulated during the liquid aspiration. The aspiration needle 1 is then removed from septum C and lowered into its washing position. At this point the aspirated liquid occupies conduit 6, 18, and 19.

Figure 2:
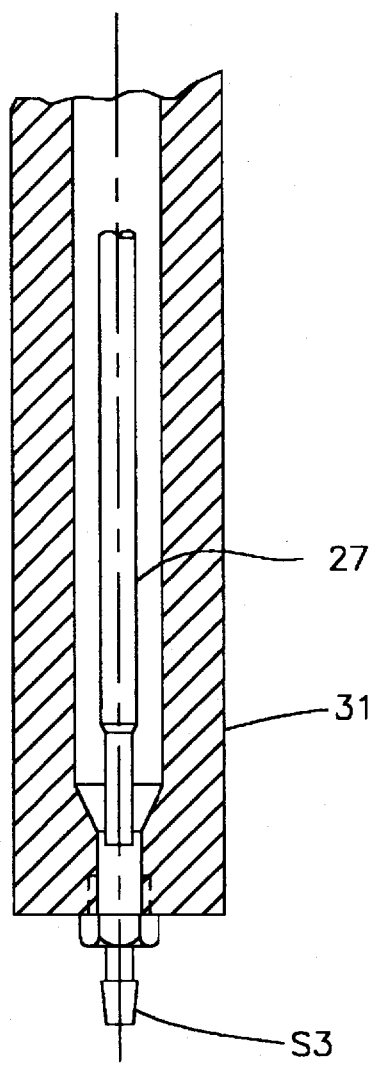
FIG. 2 is a sectional view of the waste port of the apparatus.

Refering to FIG. 2, dispense Probe 27 is then lowered into waste station 31 with mechanism 13. Waste station 31 is connected to a source of vacuum S3.

Valve 4 is then closed, valves 8 and 10 are open, and syringe 12 advances the aspirated liquid, followed by a 20 ul isolation bubble, followed by the pilot liquid through conduits 6 and 16, valve 5, conduit 17, and dispense probe 27.

Approximately 100 ul of aspirated liquid is dispensed to the waste station 31 while vacuum S3 is applied. As shown in FIG. 2, the close proximtity of the tip of dispense probe 27 to the vacuum source S3 removes any cohering liquid present on the tip of the dispense probe 27 at the end of the dispense. It is necessary to have a clean break of liquid at the tip of dispense probe 27 before dispensing to the first receiving container in order to dispense an accurate and precise amount of liquid to the first receiving container.

The dispense probe 27 then moves to the first receiving container 30. The dispense probe 27 is lowered with mechanism 13, which may be for instance a pneumatic air cylinder, so its tip is approximately 2.5 mm from the bottom of the receiving container 30, and syringe 12 advances by an accurate distance to dispense liquid to the receiving container 30.

In order to dispense an accurate and precise amount of liquid to the receiving container 30, there cannot be any liquid cohering to the probe tip after the dispense. In the prior art, a rapid deacceleration of the dispensing syringe provided the force to overcome the cohesive force holding the liquid together at the probe tip. However, a rapid dispense is required to achieve the rapid deacceleration, and a rapid dispense causes splattering and breakup of the isolation bubble referred to earlier.

If syringe 12 advances slowly to avoid splattering, liquid will be dispensed one drop at a time. A drop leaves the probe tip when the downward force of gravity on the drop overcomes the force holding the drop to the probe tip. This force is due to the cohesive force between the liquid in the drop and the liquid still within the probe tip, and to the adhesive force between the drop and the blunt face and exterior of the probe tip. By coating the blunt face and exterior of the probe tip with teflon, the adhesive force between the drop and probe is made small. Thus the force holding the drop to the probe tip is mainly due to the cohesive force between the liquid within the probe tip and the liquid within the drop. This force arises from the energy required to create an air-liquid boundary to separate the drop from the liquid within the probe tip. This energy required is equal to the air-liquid surface tension times the surface area of the air-liquid boundary formed at the probe tip when the drop breaks off. In the present instance, with a probe diameter of 0.1 cm, and a surface tension of 40 ergs/square cm, a drop size is about 15 ul. If one attempts to dispense 100 ul, then 6 drops are dispensed for a total of 90 ul, leaving 10 ul on the probe tip, as shown in FIG. 3e. Although a gentle dispense is achieved, only 90 ul of the desired 100 ul is dispensed.

During the development of this invention, it was discovered that if the distance between the probe tip and the bottom of the receiving container was kept less than the length of a drop of liquid, there was a continuous body of liquid between the probe tip and the bottom of the receiving container during the dispense. Because the receiving container 30 is wettable by the dispensed liquid (the receiving container-liquid interface has a low surface tension), the liquid preferentially adheres to the receiving container. When the dispense probe 27 rises at the end of the dispense, the preferential adhesion of the dipsensed liquid with the receiving container provides the force to overcome the cohesive force holding the liquid together at the probe tip 27, and an air-liquid boundary is formed at the probe tip.

By minimizing the probe tip diameter, and coating the exterior of the probe with a nonwettable material, the cohesive force between the liquid within the tip and the dispensed liquid is minimized, which minimizes the amount of liquid that can be dispensed.

This in turn allows an accurate and precise amount of aspirated liquid to be deposited into the receiving container 30.

Figure 3A:
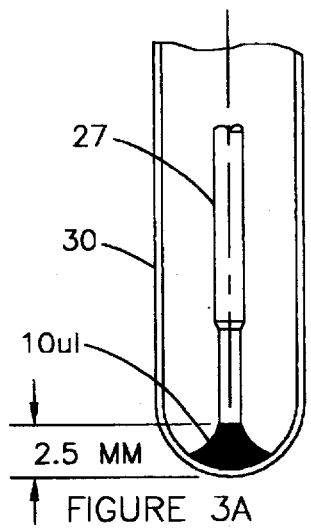
FIG. 3a is an illustration the initial shape of the dispensed liquid.
Figure 3B:
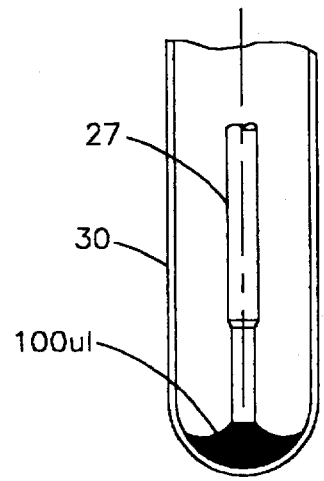
FIG. 3b is an illustration of the shape of the dispensed liquid before the dispense probe is withdrawn.
Figure 3C:
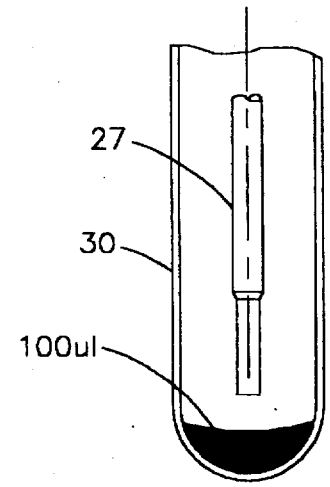
FIG. 3c is an illustration of the dispensed liquid after the dispense probe is withdrawn.
Figure 3D:
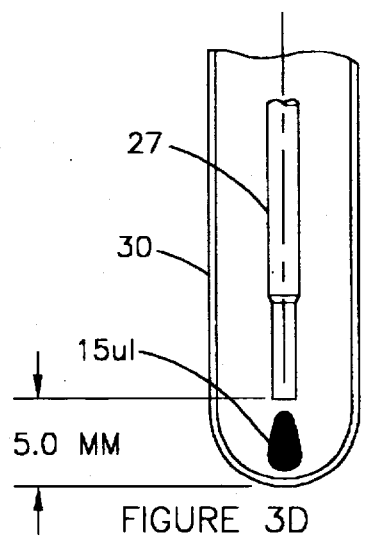
FIG. 3d is an illustration of a drop of liquid just after breaking away from the dispense probe, and just before hitting the bottom of the receiving container.
Figure 3E:
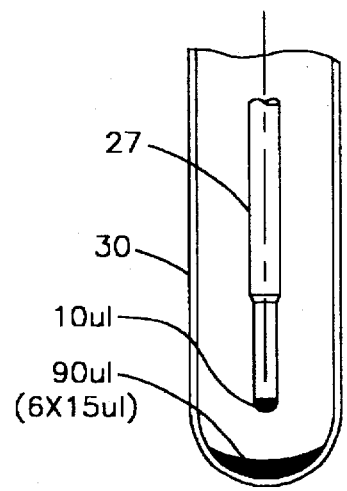
FIG. 3e is an illustration after 6 drops of liquid have been dispensed, and of residual liquid cohering to the dispense probe.

FIGS. 3a, 3b, and 3c show the sequence of events in a 100 ul dispense when the distance between the probe tip and bottom of the receiving container is less than a drop length. FIGS. 3d and e show the same 100 ul dispense sequence when this distance is greater than a drop length. In the case of blood, the length of a drop is about 3.0 mm with a dispense probe outside diameter of 0.1 cm. If the distance from the dispense probe to the bottom of the receiving container is greater than a natural drop, then 90 ul is dispensed to the receiving container (6 drops times 15 ul per drop), and the remaining 10 ul remains on the dispense probe as shown in FIG. 3e.

The minimum amount of liquid to be dispensed is set by the requirement that a continuous body of liquid bridge the gap between the dispense probe 27 and the bottom of the receiving container 30. With a 2.5 mm gap, and the liquid being blood, the minimum dispensed amount is about 10 ul.

Likewise, the dispense probe 27 may not be so low such that the surface of the dispensed liquid rises above the tip of the probe, causing liquid to adhere excessively to the outside of the probe tip. In this instance, with a 2.5 mm gap, and a receiving container with a bottom radius of curvature of 6 mm, the maximum amount of dispensed blood is approximately 100 ul, as shown in FIG. 3b. The speed of the dispense is slow enough (<200 ul/sec) to avoid splattering of liquid sample on the walls of receiving container 30. Splattered liquid on the walls of the receiving container 30 must be avoided, since the splattered liquid sample will not react with subsequent liquids added to the receiving container 30.

Figure 6:
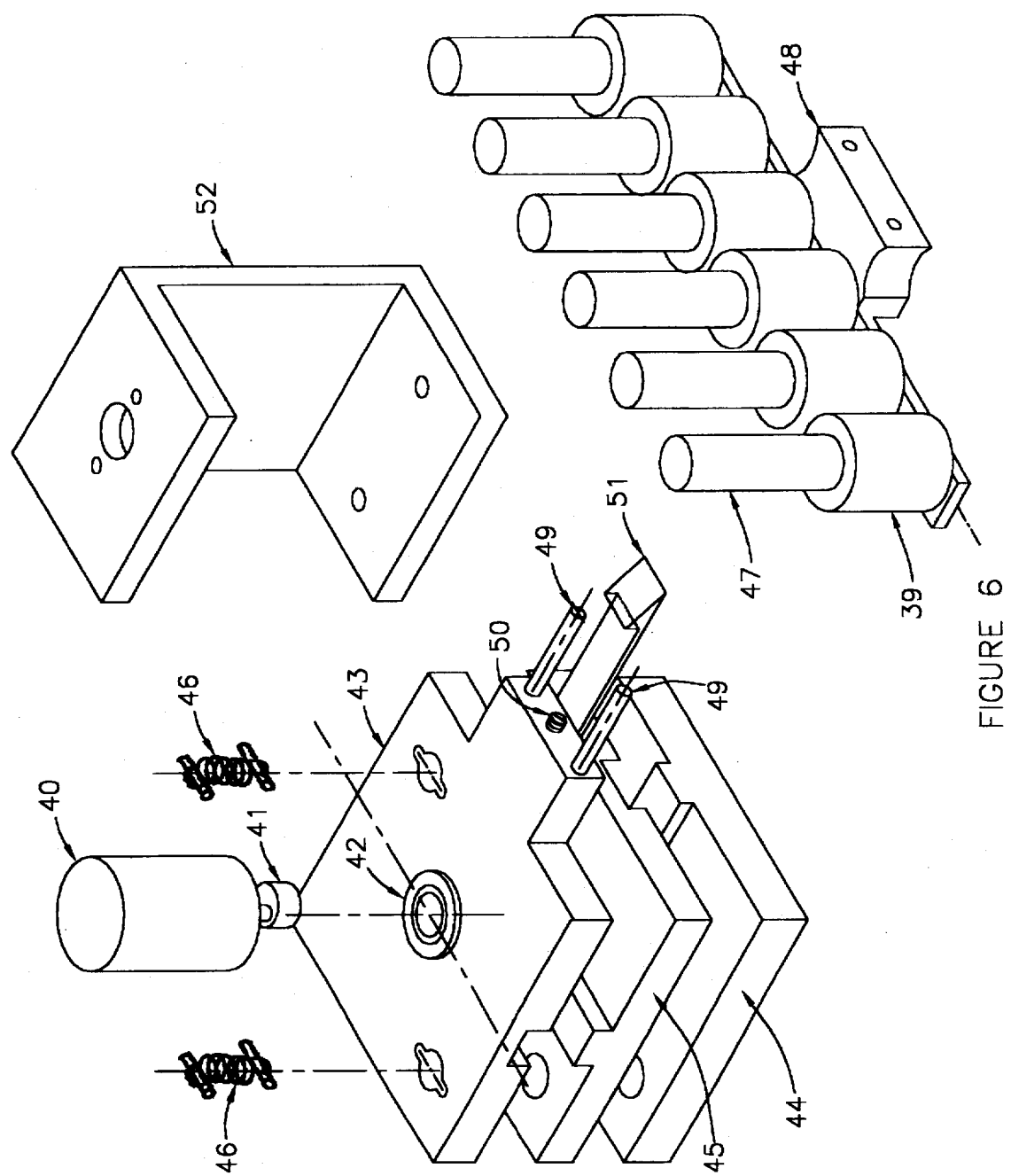
FIG. 6 is an illustration of the mixing means of multiple secondary containers.

As shown in FIG. 6, the multiple receiving containers are mounted on an apparatus that provides vortex mixing of the dispensed liquid with subsequently added reagents. The electric motor 40 rotates an eccentric hub 41 which orbits the top plate 43 via bearing 42. The orbital motion is created from two independent linear slider plates. The bottom plate 44 and middle plate 45 create an X motion, while the middle plate 45 and top plate 43 create a Y motion. The three plates are constrained in the vertical direction by the extension spring and pin assemblies 46.

The electric motor 40 and bottom plate 44 are mounted to bracket 52.

Multiple receiving containers 47 are constrained by holders 46, and said holders are rigidly attached to rack 48. Rack 48 is in turn rigidly attached to orbiting plate 43 via compression spring 50, locating pins 49, and detent lever 51, such that the orbital motion of plate 43 is rigidly transferred to receiving containers 47. This apparatus provides for vortex mixing of the contents of the receiving containers 47 about a vertical axis, which allows the dispense probe 27 unhindered access to the bottom of the receiving container.

Figure 4:
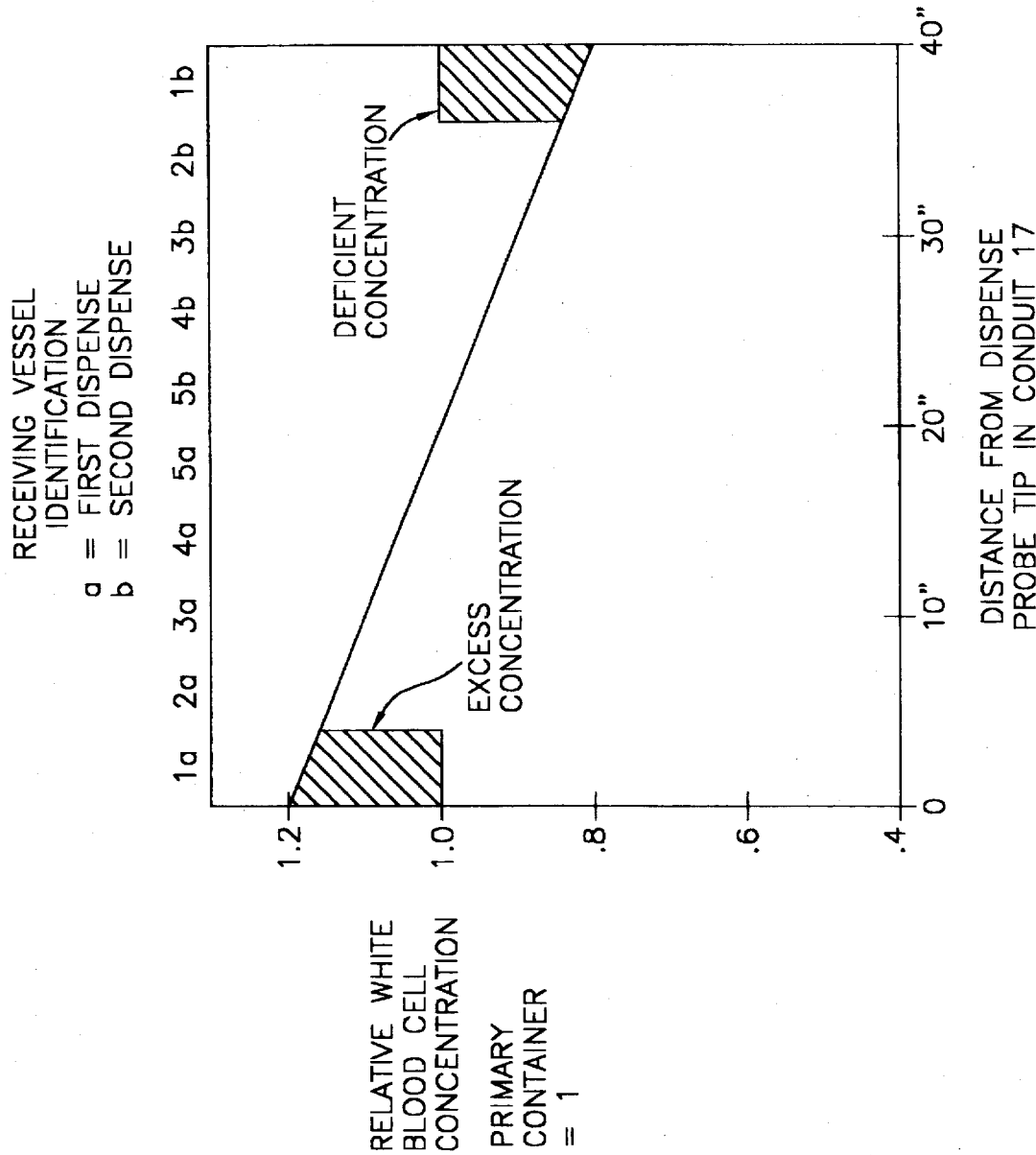
FIG. 4 is an illustration of the distribution of white blood cells within the conduit leading to the dispense probe tip, and a representation of the method of distribution of liquid to secondary containers that provides for an equal number of white blood cells in each secondary container.

The dispense probe 27 is then moved to the next receiving container, and the process can be repeated until all but approximately 100 ul of liquid remains. The last 100 ul is dispensed to waste so as not to use the liquid closest to the isolation bubble that may have become paritally diluted with pilot liquid, In the case of blood, it is desirable not only to dispense an accurate and precise amount of blood to each reaction container, but also to dispense and accurate and precise number of blood cells to each receiving container. FIG. 4 shows the distribution of white blood cells within conduit 17 and dispense probe 27 just before dispensing begins. During the advance of the blood through conduit 17, white blood cells have a higher average velocity than the average velocity of the liquid in which they reside. This is due to the tendency of the white cells to radially migrate towards the center of conduit 17 during the advance, where the liquid velocity is twice the average liquid velocity. Thus the leading volume of blood contains a higher concentration of white blood cells than the trailing volume. In order to dispense equal numbers of white blood cells to each receiving container, it is necessary to dispense the first half of the desired volume to the first receiving container (volume 1a), the first half to the second container (volume 2a), repeating this until the last receiving container (volume 5a). Then it is necessary to dispense the second half to the last receiving container (volume 5b), then dispense the second half to the next to the last receiving container (volume 4b), and so on, until the second half is dispensed to the first receiving container (volume 1b). As shown in FIG. 4, the excess concentration of white cells in volume 1a is balanced by the deficient concentration of white cells in volume 1b.

This method provides for the equal distribution of white blood cells to multiple receiving containers, such that each receving container contains a representative number of white cells per unit volume characteristic of the blood within the sealed container 29.

After dispensing is completed, the dispense probe 27 is lowered into the waste station 31, and valve 10 is closed, valve 11 is open, and pilot liquid is aspirated by syringe 12 from S2. Valve 10 is then open, valve 11 is closed, and the pilot liquid is dispensed through conduit 22, valve 10, conduit 21, Valve 8, conduits 20, 6, and 16, valve 5, conduit 17, and dispense probe 27, thereby flushing out any dispensed liquid remaining within these conduits.

The tip of dispense probe 27 is in close association with waste station 31 such that the pilot liquid comes up and around the outside of the dispense probe 27 to clean the outside of the dispense probe 27. Vacuum S3 is then applied to waste station 31 to dry the outside of the dispense probe 27.

Valve 5 and 10 are then closed. Valve 4 and 11 are open, and syringe 12 aspirates pilot liquid from S2. Valve 10 is then open, valve 11 is closed, and syringe 12 dispenses pilot liquid through conduit 22, valve 10, conduit 21, valve 8, conduits 20, 6, and 15, valve 4, conduit 14, filter 3, and aspirating needle 1, thereby flushing out any dispensed liquid remaining within these conduits.

With the aspirating needle 1 in its wash position, the pilot liquid dispensed is pulled down around the outside of the aspirating needle by a vacuum, so as to clean the exterior as well as the interior of the needle.

Valves 4 and 8 are then closed, valves 5 and 7 are open, and a vacuum is applied to S1 by known methods of the art. This causes the pilot liquid remaining in the dispense probe 27, conduits 17, 16 and 6 to be sucked into resevoir 25. It also causes residual sample liquid in conduits 18, 19, and 26 to be sucked into reservoir 25. Valve 5 is then closed, and valve 4 is open. This causes the pilot liquid remaining in the aspiration needle 1, conduits 14 and 15 to be drawn through conduits 6 and 18, valve 7, conduits 19 and 26 to reservoir 25.

The application of vacuum S1 to aspiration needle 1, conduits 15, 16, 17, 6, and 18, and dispense probe 27 dries the path the next aspirated liquid will take, thereby causing the aspirated liquid in the next aspiration cycle not to be diluted by residual pilot liquid. In the case of blood, this is necessary to assure the receiving containers contains the same number of white cells per unit volume characteristic of the blood within the sealed container 29.

At this point, there is a air/liquid 28 interface at the junction of conduits 18 and 20, and the entire process of aspirating and dispensing blood can be repeated.

We claim:

1. An apparatus for undiluted aspirating and dispensing of liquids, comprising:

a conduit system including an aspiration path and a dispense path, said aspiration path including a portion of said dispense path;

means for cleaning and drying said aspiration and dispense paths prior to aspiration of said liquid;

aspirating means for undiluted aspirating said liquid from a sample vessel into and along said aspiration path including said dispense path portion of said aspiration path, said paths being cleaned and dried prior to said aspiration of said liquid;

dispensing means for undiluted dispensing said liquid along and out of said portion of said dispense path and into at least one receiving vessel; and gaseous pushing means intersecting said dispense path at one end thereof and for generating a gaseous interface at said dispense end and pushing said liquid in front of said gaseous interface along and out of said dispense path and into said at least one receiving vessel.

2. The apparatus for undiluted aspirating and dispensing of liquids according to claim 1 further including:

a first Y junction of first, second and third conduits;

and wherein said aspirating means includes a means for filling said first and third conduits with said liquid in an undiluted state;

and further wherein said dispensing means includes means for filling said second conduit with a pilot fluid;

and further wherein said gaseous pushing means includes means for providing a gaseous interface between said liquid and said pilot fluid at said first Y junction.

3. The apparatus for undiluted aspirating and dispensing of liquids according to claim 2 further including a second Y junction of fourth, fifth and sixth conduits wherein said third and sixth conduits are disposed in fluid communication to provide both an aspirating and a dispensing path to said third conduit of said first Y junction.

4. The apparatus for undiluted aspirating and dispensing of liquids according to claim 3, further including first, second, third and forth valve means disposed on said first, second, forth and fifth conduits respectively, to provide for opening and closing said conduits to control the flow of said liquid, said pilot fluid and said gaseous interface within said first and second Y junctions and said first through sixth conduits.

5. The apparatus for undiluted aspirating and dispensing of liquids according to claim 4 further including a light refractive and transmissive fluid sensing means for sensing fluids within said first conduit; said sensing means, said first, second third and forth valve means, and said first, third, forth, and sixth conduits cooperating to provide isolation and storage means for isolating and storing a predetermined amount of said liquid and isolating it from contamination and dilution by means of said gaseous interface between said liquid and said pilot fluid at said first Y junction.

6. The apparatus for undiluted aspirating and dispensing of liquids according to claim 5 wherein each of the aspirating, dispensing and storing means include a liquid path, and wherein each of said aspirating and dispensing means include a probe means and a vacuum generating means in vacuum communication therewith disposed at a terminating end of each of said liquid paths and further including liquid path preparation means for cleaning and drying all of said aspirating, dispensing and storing means liquid paths by the application of vacuum along said liquid paths to at first flush said liquid paths with pilot fluid, then clean and dry said liquid paths by causing air to flow therethrough, said first, second, third and fourth valve means, and said first, second, third, fourth, fifth and sixth conduits cooperating to provide said application of vacuum, air and pilot fluid flush through said liquid paths.

7. The apparatus for aspirating and dispensing liquids of claim 1 wherein the dispensing means includes:

a wettable vessel and a non wettable dispense probe tip for depositing said liquid into said receiving vessel such that when said liquid is terminated and said non wettable dispense probe is separated fom the previously dispensed liquid, then the energy of the preferential association of said liquid with said wettable vessel overcomes the internal skin effect energy of the liquid and causes an air/liquid interface at the probe tip.

8. The apparatus for aspirating and dispensing liquids of claim 7 further including:

cleaning means for introducing cleaning fluid into said apparatus;

a positive displacement pump means and negative vacuum pump means for moving said liquid and said cleaning fluid throughout said apparatus;

conduit means for interconnecting said aspirating, dispensing; isolating and storage, cleaning and pump means; and valve means for directing said liquid and said cleaning fluid through said conduit means and said aspirating, dispensing, isolating and storage means, wherein said isolation and storage means for storing a predetermined amount of said liquid and isolating it from contamination by means of said gaseous interface includes a liquid sensor disposed at a first predetermined position in said conduit means, and wherein said pump means and valve means cooperate to provide said gaseous interface at a second predetermined position in said conduit so as to isolate said predetermined amount of liquid.

9. The apparatus for aspirating and dispensing liquids of claim 8 wherein said sensor includes a light sensitive means capable of distinguishing air, serum and blood based on their transmitting and refracting of light due to their respective indices of refraction.

10. The apparatus for aspirating and dispensing liquids of claim 9 wherein said aspirating means for aspirating liquid from said sample vessel includes a piercing needle and a septum, and means for raising said piercing needle so as to pierce through said septum.

11. The apparatus for aspirating and dispensing liquids of claim 10 further including sterilizing means for at first flushing with cleaning fluid and then vacuum drying both said aspirator means and said dispensing means so as to prevent dilution and contamination of said liquids.

12. The apparatus for aspirating and dispensing liquids of claim 7 further including equivalating means for providing multiple equivalent dispensed samples of a predetermined amount of liquid by dispensing at first one half of a sample in the order sample a, sample a+1, sample a+2, sample a+3 ..., sample a+n, and then dispensing the second half of said sample in the reverse order sample a+n, ... sample a+3, sample a+2, sample a+1 and sample a.

13. The apparatus for aspirating and dispensing liquids of claim 12 wherein said liquids may be blood, serum, saliva, urine, and chemical liquids.

14. The apparatus for aspirating and dispensing liquids of claim 1 further including vertical axis mixing means for vortex rotating the receiving vessel about the vertical axis of said receiving vessel while maintaining the opening portion of said receiving vessel within a predetermined annular radius so that said receiving vessel is always in the proper location for the next dispense operation.

15. Apparatus for undiluted aspirating and dispensing of liquids, comprising:

a conduit system including an aspiration path and a dispense path, said aspiration path including a portion of said dispense path;

aspirating means for aspirating of liquid from a sample vessel into and along said aspiration path including said dispense path portion of said aspiration path;

dispensing means for dispensing said liquid along and out of said portion of said dispense path and into at least one receiving vessel; and contamination prevention means for insuring that no contamination including dilution occurs within said fluid conduit paths including cleaning/drying means for cleaning and drying said fluid conduit paths prior to aspiration of said liquid and means for moving said liquid along the dispensing path without contamination or dilution.

16. The apparatus for undiluted aspirating and dispensing of liquids of claim 15, wherein said fluid conduit paths include first and second ends and wherein said cleaning/drying means includes purging means for applying a vacuum to one end of each of said fluid conduit paths while venting the other end of each of said fluid conduit paths to atmosphere for at first removal of fluids within said fluid conduit paths and then air drying of each of said fluid conduit paths.

17. The apparatus for undiluted aspirating and dispensing of liquids of claim 16 wherein said means for moving said liquid along the dispensing path without contamination or dilution includes non-dilution means for generating a gaseous interface between said liquid and a pilot fluid at a predetermined midway location to provide a pilot fluid-gaseous interface-liquid sequence at the beginning of and within said dispensing path and thereafter pushing said liquid along said dispensing path by said pilot fluid-gaseous interface-liquid sequence such that said liquid never contacts said pilot fluid.

18. The apparatus for undiluted aspirating and dispensing of liquids of claim 17 wherein said non-dilution means includes a first Y junction of first, second and third conduits and a means for filling said first and third conduits with said liquid in an undiluted state; and further including means for filling said second conduit with a pilot fluid and means for providing a gaseous interface between said liquid and said pilot fluid at said first Y junction.

19. The apparatus for undiluted aspirating and dispensing of liquids according to claim 18 further including a second Y junction of fourth, fifth and sixth conduits wherein said third and sixth conduits are disposed in fluid communication.

* * * * *